US011272974B2

(12) United States Patent
Capart

(10) Patent No.: US 11,272,974 B2
(45) Date of Patent: Mar. 15, 2022

(54) ELECTRO-CHEMICAL SURGICAL INSTRUMENT

(71) Applicant: AUXIN SURGERY, Louvain-la-Neuve (BE)

(72) Inventor: Gilles Capart, Louvain-la-Neuve (BE)

(73) Assignee: AUXIN SURGERY, Louvain-la-Neuve (BE)

( * ) Notice: Subject to any disclaimer, the term of this patent is extended or adjusted under 35 U.S.C. 154(b) by 73 days.

(21) Appl. No.: 16/309,633

(22) PCT Filed: Jul. 26, 2017

(86) PCT No.: PCT/EP2017/068886
§ 371 (c)(1),
(2) Date: Dec. 13, 2018

(87) PCT Pub. No.: WO2018/019885
PCT Pub. Date: Feb. 1, 2018

(65) Prior Publication Data
US 2019/0262059 A1 Aug. 29, 2019

(30) Foreign Application Priority Data
Jul. 28, 2016 (EP) .................................... 16181762

(51) Int. Cl.
*A61B 18/06* (2006.01)
*A61B 18/14* (2006.01)
*A61B 18/00* (2006.01)

(52) U.S. Cl.
CPC .............. *A61B 18/06* (2013.01); *A61B 18/14* (2013.01); *A61B 18/1442* (2013.01);
(Continued)

(58) Field of Classification Search
CPC .......... A61B 18/06; A61B 2018/00922; A61B 2218/002; A61B 2018/00607;
(Continued)

(56) References Cited

U.S. PATENT DOCUMENTS 5,282,799 A * 2/1994 Rydell ............... A61B 18/1402
604/35
5,366,476 A * 11/1994 Noda .................. A61B 17/2909
606/206
(Continued)

FOREIGN PATENT DOCUMENTS

EP 2896379 A1 7/2015
WO 2008072237 A2 6/2008
(Continued)

OTHER PUBLICATIONS

European Search Report dated Jan. 16, 2017 for European Application No. 16181762 filed Jul. 26, 2017.
(Continued)

*Primary Examiner* — Amber R Stiles
*Assistant Examiner* — Avery Smale
(74) *Attorney, Agent, or Firm* — Blue Filament Law PLLC

(57) ABSTRACT

An electro-chemical surgical knife is detailed that in a single instrument provides both a chemically assisted mechanical dissector and an electrical knife. The chemically assisted mechanical dissector: includes a conductive mechanical instrument, a source (7) of a cleavage solution, a pump (8) for feeding the cleavage solution to, a channel (2) for transporting the cleavage solution to an operating location, and a flow controller (8c) for controlling the feeding of the cleavage solution by the pump to an inlet of the channel. The electric knife includes a source of high frequency AC electrical power (5) for feeding AC current through an
(Continued)

electric conductor (3) to, an electrode (6) formed by the conductive mechanical instrument and further comprises a second controller (5c) for controlling the feeding of the AC current to the electrode.

12 Claims, 5 Drawing Sheets

(52) U.S. Cl.
CPC ....... *A61B 18/1402* (2013.01); *A61B 18/1445* (2013.01); *A61B 18/1482* (2013.01); *A61B 18/1492* (2013.01); *A61B 2018/00595* (2013.01); *A61B 2018/00601* (2013.01); *A61B 2018/00607* (2013.01); *A61B 2018/00922* (2013.01); *A61B 2018/00982* (2013.01); *A61B 2018/00994* (2013.01); *A61B 2018/068* (2013.01); *A61B 2018/1412* (2013.01); *A61B 2018/1417* (2013.01); *A61B 2018/1422* (2013.01); *A61B 2218/002* (2013.01)

(58) Field of Classification Search
CPC . A61B 18/14; A61B 18/1412; A61B 18/1442; A61B 2018/00595; A61B 2018/00601; A61B 2018/00982; A61B 2018/00994; A61B 2018/1422; A61B 18/1402; A61B 18/1445; A61B 18/1482; A61B 18/1492; A61B 2018/00011; A61B 2018/00005; A61B 2018/00916; A61B 2018/0225; A61B 18/082; A61B 18/085; A61B 2018/1452; A61M 25/0067; A61M 25/0082; A61M 2205/051; A61M 2205/3626

See application file for complete search history.

(56) References Cited

U.S. PATENT DOCUMENTS

| | | | |
|---|---|---|---|
| 2001/0032002 A1* | 10/2001 | McClurken | A61B 18/1445 607/103 |
| 2002/0062123 A1* | 5/2002 | McClurken | A61B 18/1442 606/34 |
| 2005/0251134 A1 | 11/2005 | Woloszko et al. | |
| 2008/0195090 A1 | 8/2008 | Takashino et al. | |
| 2010/0204688 A1* | 8/2010 | Hoey | A61B 18/18 606/27 |
| 2011/0112434 A1 | 5/2011 | Ghabrial et al. | |
| 2012/0253192 A1* | 10/2012 | Cressman | A61M 39/0247 600/431 |

FOREIGN PATENT DOCUMENTS

| | | |
|---|---|---|
| WO | 2008129016 A1 | 10/2008 |
| WO | 2009009274 A2 | 1/2009 |
| WO | 2010118818 A1 | 10/2010 |
| WO | 2014180902 A1 | 11/2014 |
| WO | 2015052320 A1 | 4/2015 |

OTHER PUBLICATIONS

International Search Report dated Oct. 26, 2017 for International Application No. PCT/EP2017/068886 filed Jul. 26, 2017.

* cited by examiner

ELECTRO-CHEMICAL SURGICAL INSTRUMENT

CROSS REFERENCE TO RELATED APPLICATIONS

This application is a 35 U.S.C. § 371 Application of International Application Number PCT/EP2017/068886 filed 26 Jul. 2017, and claims priority benefit of European Application Number EP16181762.2 filed 28 Jul. 2016, the contents of which are hereby incorporated by reference.

FIELD OF THE INVENTION

The present invention relates to the field of surgical cutting instruments and, in particular to electro-chemical surgical instruments combining an electric knife and a chemically assisted mechanical dissector in a single instrument. The present invention allows the sequential or simultaneous use with a single instrument of an electric knife and of a chemically assisted mechanical dissector including the delivery to a conductive mechanical instrument of a cleavage solution able to break disulphide bonds of polypeptide chains and proteins. A surgeon needs not replace the electro-chemical surgical instrument to switch from an electrical cutting mode of tissues to a chemical debonding mode of tissues, or for combining both simultaneously, depending on the instantaneous surgical conditions better suited for one or the other type of knife. The two knives can also be used simultaneously to yield enhanced efficacy of removal of target tissues over the use of each knife individually.

BACKGROUND OF THE ART

Instruments such as electric knives are used in all types of surgery including open, laparoscopic, and endoscopic surgeries to cut by burning and/or to cauterize tissue. These electric knives are connected to a source of radio frequency AC electrical power for supplying electric current to one or more electrodes. The frequency and power of the electric current can be regulated to switch between a cutting mode and cauterizing mode.

An electric knife usually comprises one electrode (monopolar knives) or two electrodes (bipolar knives). In the case of a monopolar knife, a return electrode is usually applied on the skin of a patient. It also comprises an electric conductor extending from a connection end comprising a connector for connecting the electric conductor to the source of high frequency AC electrical power, to an electrode end comprising the electrode. This electric conductor is housed in a non-conductive housing. Electric knives selectively remove tissue by contacting and electrically burning them. In laparoscopic and open surgeries, which afford greater control in all directions of the instruments than in endoscopic surgery, the geometries of the electrodes can be chosen such as to yield great accuracy in the cutting/burning of tissues. In spite of such accuracy, removal of tissues with electric knives can be traumatic and can provoke hemorrhages. By tuning the AC electric power supplied to the electrode, an electric knife can also be used to cauterize bleeding wounds.

Patent application WO2014180902 describes a chemical dissector or chemical knife, that uses a source of a cleavage solution comprising a substance, referred to as cleavage solution, able to break disulphide bonds of polypeptide chains and proteins. The cleavage solution described in said document is sodium 2-mercatoethanesulfonate (MESNA). By breaking the disulphide bonds of polypeptide chains and proteins, a cleavage solution such as MESNA can chemically disrupt such bonds binding tissues together and separate them along pre-existing planes of cleavage without cutting. This way tissues can be smoothly separated along such planes of cleavage without damaging critical organs, such as veins, nerves, or muscles, and reducing the risks of relapse from pathologic material left behind. Furthermore, hemorrhages are reduced or even eliminated. This is advantageous in that the operation is simplified by maintaining a good visibility of the operating space throughout the operation and in that the side effects from surgery are reduced. The separation pattern obtained with chemical dissectors, however, cannot be controlled freely, as it must follow pre-existing natural planes of cleavage between the tissues.

Patent EP2419038 describes an electric knife comprising a fluid jet device for spraying a liquid blade at high pressure. The liquid blade is suitable for hydro-mechanically cutting tissues. The supply line that guides the jet flow is directed ahead of an electrode and is dispensed from a nozzle located downstream of the electrode. The use of a fluid jet described in said document cannot be defined as a chemical dissector, but rather as a hydro-mechanical knife, since the action of the liquid jet on the tissues is purely mechanical. As such, it suffers of similar pros and cons as electric knives and conventional knives, in that the cut can be controlled very accurately, but can damage critical organs, be traumatic, and provoke hemorrhages, which blur the vision of the surgeon, must be cauterized, and leave a scar.

Patent application EP2896379 describes a high frequency electric knife comprising a conduit line for supplying a liquid to an electrode end. The conduit line passes through the electrode and guides the liquid that is projected ahead of the electrode in order to clean the operation area from blood, loose tissues, etc. This solution improves the visibility of the surgeon throughout the duration of the operation, but does not contribute to cutting any tissue.

Patent application WO2009009274 describes an instrument for performing submucosal medical procedures in a desired area of the digestive tract using endoscopy. Said instrument includes one or more of a safe access needle injection instrument, a submucosal tunneling instrument, a submucosal dissection instrument including an electric knife, a mucosal resection device.

Although an electric knife burns rather than actually cutting the tissues it contacts, the term "cut" and derivatives thereof are used herein indiscriminately to refer to any of tissue burning with an electric knife, as well as slicing through tissues with a conventional knife or a hydro-chemical dissector. By contrast, the term "cut" cannot be used for chemical dissectors, because separation of tissues occurs by detaching a target tissue from a healthy tissue after disruption of specific chemical bonds, and all tissues or vessels comprising no such bonds remain unaffected by the cleavage solution. In summary, target tissues can be separated from healthy tissues by cutting them with an electric knife or a scalpel, or by detaching them by use of a cleavage solution. As discussed supra, both operations of cutting and detaching target tissues have their pros and cons.

In a totally different technical field from electro-chemical surgical instruments, patent application WO2008072237 describes a device for hair removal and skin treatment including a dispensing unit for dispensing a depilatory substance onto the skin and RF electrodes for applying RF energy to the substance treated skin. The RF electrodes are used for inducing a heat treatment to the skin to promote the action of the applied depilatory substance. The RF electrodes do not form an electric knife and said device is not an electro-chemical surgical instrument, as the treatment is entirely applied to the surface of the skin.

There remains a need in the art for a surgical instrument suitable for separating tissues accurately e.g., by cutting or detaching tissues, and yet minimizing the traumatisms and hemorrhages during a cutting operation. The present invention proposes such surgical instrument. This and other advantages of the present invention are described in more details in the next sections.

SUMMARY OF THE INVENTION

The present invention is defined in the appended independent claims. Preferred embodiments are defined in the dependent claims.

The present invention concerns an electro-chemical surgical instrument for use in surgery for cutting, cauterizing, and/or chemically removing a target tissue in an operating site, said electro-chemical surgical instrument comprising:
(A) A chemically assisted mechanical dissector for removing a target tissue, comprising:
  (a) a conductive mechanical instrument coupled to a distal end of,
  (b) a tube (1t) which is non-conductive and extends over a length, L1, measured parallel to a longitudinal axis, Z, from a proximal end to the distal end;
  (c) a source (8) of a cleavage solution able to break disulphide bonds of polypeptide chains and proteins, which is fluidly coupled through a pump to an inlet of,
  (d) a channel (2) extending from an inlet (2i) to one or more channel outlets (2o), having a housed portion of length, L2, which is housed in the tube with said one or more channel outlets being located at or adjacent to the distal end, such as to allow the wetting of a surface of the conductive mechanical instrument with the cleavage solution when the pump is activated;
  (e) a flow controller (8c) configured for activating the pump and thus feeding the cleavage solution to the channel outlet; and
(B) An electric knife for cutting and/or cauterizing a target tissue, comprising:
  (f) an electric conductor (3) extending from a connection end comprising a connector (4) for connecting the electric conductor to a source (5) of high frequency AC electrical power, for feeding electric power to an electrode end comprising an electrode (6) formed by the conductive mechanical instrument, wherein a portion of said electric conductor is housed in the tube
  (g) an electric controller (5c) configured for controlling the feeding of current to the electrode.

In a preferred embodiment, the surface of the conductive mechanical instrument is a lateral surface which is non-normal preferably substantially parallel, to the longitudinal axis. The one or more outlets generally do not form needles. Said one or more channel outlets of the chemically assisted mechanical dissector are preferably oriented such as to dispense the cleavage solution onto said at least one lateral surface. The conductive mechanical instrument forming the electrode can have one of the following geometries:
(a) comprising a cylindrical portion defining the lateral surface and a distal end portion in the shape of a spherical or elliptical cap or (b) comprising two lateral surfaces separated from one another by the thickness of the electrode and forming a spatula The electro-chemical surgical instrument can be equipped with a monopolar or a bipolar electric knife. A monopolar electric knife comprises a single electrode at the electrode end of the electric conductor. By contrast, a bipolar knife further comprises a return electrode located at a return electrode end of a return electric conductor forming together with the electrode at the electrode end of the electric conductor an electric circuit coupled to the source of high frequency AC electrical power. The electric controller preferably comprises a switch trigger, more preferably a footswitch, for controlling the feeding of electric current to the electrode. The electro-chemical surgical instrument can further comprise a handle, wherein the switch trigger is a pushbutton switch located on the handle.

The conductive mechanical instrument may comprise a pair of first and second jaw members, at least one of the first and second jaw members being movable from an open configuration to a clamping configuration, the first jaw member including the electrode, thus forming monopolar electrosurgical forceps or a monopolar Maryland dissector. If the second jaw member includes a return electrode, bipolar electrosurgical forceps or a bipolar Maryland dissector are thus formed.

The cleavage solution can be selected form sodium 2-mercatoethanesulfonate (MESNA), dithiothreitol (DTT), β-mercaptoethanol or free cysteine. The flow controller may comprise a flow trigger, preferably a footswitch, for controlling the pump or a valve located downstream from the pump, to feed the cleavage solution to the channel outlet. The electro-chemical surgical instrument may further comprise a handle, wherein the flow trigger is a pushbutton switch located on the handle. The pump can be selected from a peristaltic pump, a syringe or piston pump. The pump pressurizes the cleavage solution at a maximum pressure of preferably not more than 2 bar.

For open surgery and laparoscopic surgery, the tube of the chemically assisted mechanical dissector can be at least partly rigid. For endoscopic surgery, the tube is preferably flexible to run freely in a lumen of an endoscope.

The present invention also concerns a method for delivering a cleavage solution as defined supra, which is stored in a source of cleavage solution, to the conductive mechanical instrument of an electro-chemical surgical instrument according to anyone of the preceding claims, said method comprising the following steps:
(a) providing an electro-chemical surgical instrument according to anyone of the preceding claims;
(b) connecting the connection end of the electric conductor to a source of high frequency AC electrical power (5);
(c) by means of the flow controller (8c), actuating the pump (8) or a valve (8v) located downstream from the pump to feed the cleavage solution from the source of cleavage solution to the outlet of the channel and to the conductive mechanical instrument.

The present invention also concerns a method for separating target tissues from an organ, said method comprising the following steps:
(a) providing an electro-chemical surgical instrument according to claim 1;
(b) connecting the electrode to the source of high frequency AC electrical power;

(c) bringing the conductive mechanical instrument of the electro-chemical surgical instrument to an operating site including the target tissues;

(d) without removing the conductive mechanical instrument from the operating site, sequentially or simultaneously,
   (i) actuating the electric controller to feed electric current to the electrode formed by the conductive mechanical instrument, in order to, at least partially, electrically cut or cauterize a target tissue, and;
   (ii) actuating the flow controller to feed the cleavage solution from the source of cleavage solution to the outlet of the channel and onto a surface of the conductive mechanical instrument, in order to, at least partially, chemically separate a target tissue.

In one embodiment, the method further comprises the following steps:

(a) forming a pre-cut at a specific location of the organ with the electrode; followed by, (b) dispensing cleavage solution into the pre-cut for chemically separating a target tissue from the organ along a plane of cleavage adjacent to the pre-cut.

In an alternative embodiment, the method further comprises the following steps:

(a) dispensing cleavage solution onto a specific location of the organ in order to form a gap between a target tissue and a rest of the organ; followed by, (b) burning the target tissue with the electrode keeping the rest of the organ thermally insulated by the gap.

BRIEF DESCRIPTION OF THE DRAWINGS

These and further aspects of the invention will be explained in greater detail by way of example and with reference to the accompanying drawings in which.

DETAILED DESCRIPTION OF THE INVENTION

Figure 1:
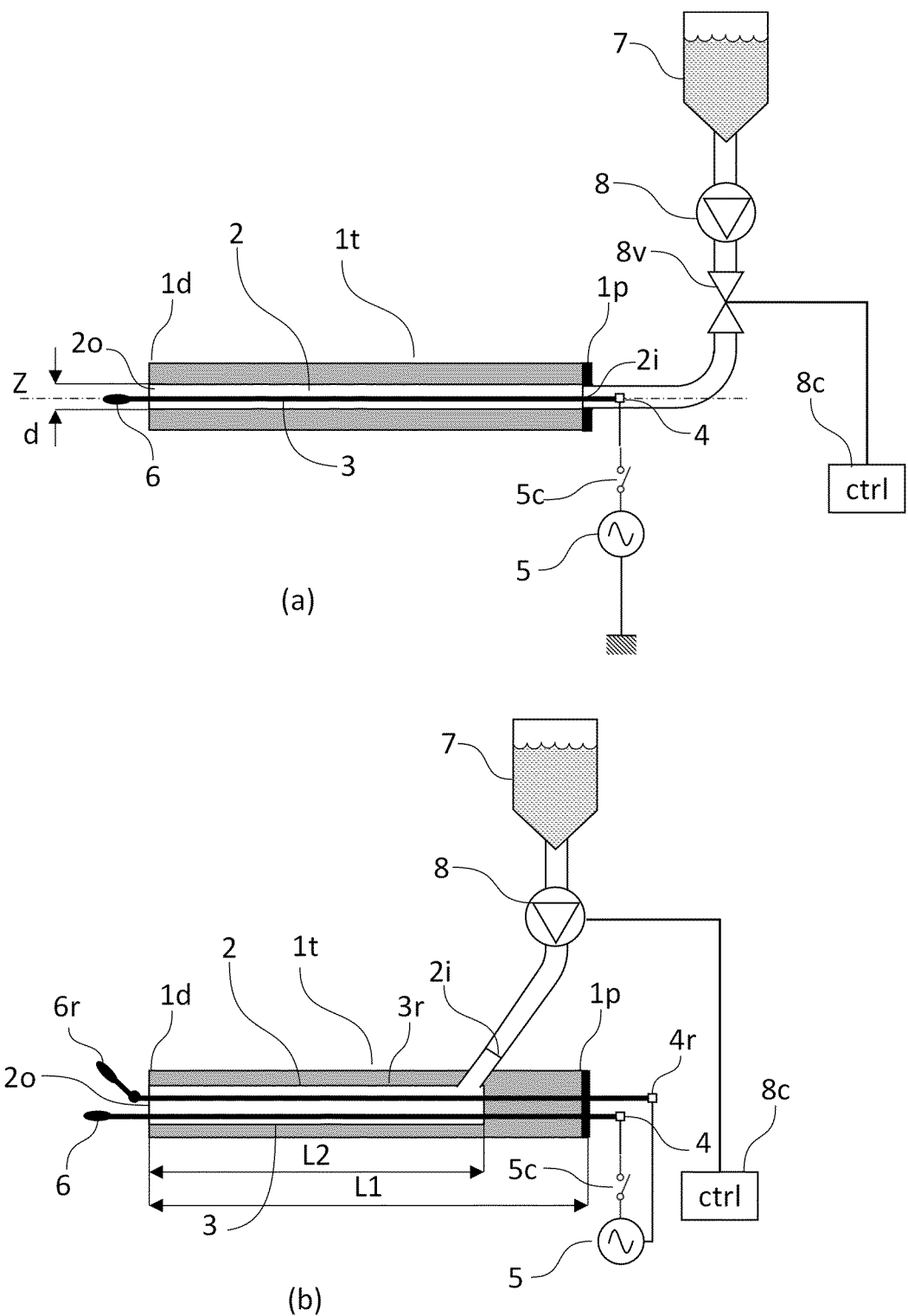
FIG. 1 shows embodiments of electro-chemical dissectors according to the present invention, (a) shows a monopolar knife and (b) a bipolar knife.

FIGS. 1(a) and (b) shows embodiments of an electro-chemical surgical instrument according to the present invention. This instrument comprises a chemically assisted mechanical dissector provided with a tube, 1t, which is non-conductive and extends over a length, L1, measured parallel to a central axis, Z, from a proximal end, 1p, to a distal end, 1d. Besides elements of the chemical dissector, the tube may house elements of electric knife. A conductive mechanical instrument for cutting or detaching tissues of both electric knife and chemically assisted mechanical dissector is coupled to the tube, adjacent to the distal end of the tube which can be brought by a surgeon at the operation location. The position of the distal end can be handled by the surgeon either directly by handling the tube, or through a handle (cf. FIG. 2), or through an endoscope (cf. FIG. 4).

The chemically assisted mechanical dissector is formed by:
   a source, 7, of cleavage solution,
   a pump, 8, for feeding the cleavage solution to,
   a channel, 2, for transporting the cleavage solution to the operating location,
   a conductive mechanical instrument, and
   a flow controller, 8c, for controlling the volumetric feeding of cleavage solution by the pump to the channel inlet.

The channel, 2, extends from a channel inlet, 2i, to one or more channel outlets, 2o, and is partially housed in the tube, thus defining a housed portion of length, L2. The outlet(s) of the channel is located at or adjacent to the distal end of the tube. The downstream portion of the channel, 2, including the outlet(s), 2o, does not form a needle and cannot be inserted through a tissue. Instead, the channel outlet(s) is provided such as to wet a surface of a conductive mechanical instrument when the pump is actuated. The conductive mechanical instrument can have cutting edges and/or blunt edges, or may have no edges. It can have a geometry of revolution. Geometries of the conductive mechanical instrument are described below.

The source of a cleavage solution, 7, can be a cartridge, a bag, a vessel, or a syringe containing a cleavage solution which is able to break disulphide bonds of polypeptide chains and proteins. The source of cleavage solution is fluidly coupled to the inlet of the channel through a pump, 8. If the cleavage solution is contained in a syringe, the syringe forms both the source of cleavage solution and the pump. A dispensing tube fluidly couples the source of cleavage solution and pump to the inlet of the channel.

The flow controller, 8c, allows the accurate control by the surgeon of the volume of cleavage solution dispensed at any moment of the operation. As discussed in continuation, it is generally in the form of a foot pedal, or a finger trigger. As shown in FIG. 1(b) the controller may control the actuation of the pump or, alternatively, as shown in FIG. 1(a), it can actuate a valve, 8v, disposed downstream from the pump.

The electric knife is formed by:
   A source of high frequency AC electrical power, 5, for feeding AC current through
   An electric conductor, 3, to,
   An electrode, 6, formed by the conductive mechanical instrument, and further comprises
   A second controller, 5c, for controlling the feeding of electric current to the electrode.

The source of high frequency AC electric power, 5, can generate high frequency current at a frequency comprised between 1 k Hz and 1 MHz. The absolute value of the applied voltage may be lower than 200 V for cauterising; it may be comprised between 200 V and 1 kV for cutting by vaporization; and it can be more than 1 kV for burning a large area.

The electric conductor, 3, extends from a connection end to an electrode end. The connection end of the conductor comprises a connector, 4, for connecting the electric conductor to the source of high frequency AC electrical power 5. The electrode end comprises an electrode, 6, formed by the conductive mechanical instrument The electric conductor can be housed, at least partially, in a portion of the length of the tube with the electrode end thereof being located outside from and adjacent to the distal end, and adjacent to the channel outlet. The housed portion of the electrical conductor can extend in the channel, 2, or in separate lumen.

As briefly discussed supra, the electrode, 6, formed by the conductive mechanical instrument can have various geometries which are discussed in continuation, depending on the type of tissue to be removed, and on the type of surgery applied (endoscopic electrodes substantially differ from electrodes for laparoscopic or open surgery, because the angular orientation about the axis, Z, of an endoscopic electrode is more difficult to control).

The electric controller, 5c, allows the control of the feeding of current to the electrode. It can be an on/off switch or a variable switch (or dimmer). It can be controlled for example by means of a foot pedal or a finger trigger.

The conductive mechanical instrument is brought at the operating location inside the patient. It is coupled to the distal end of the tube, which is the tube end located furthest from the source of the cleavage solution and furthest from the source of high frequency AC electrical power. The proximal end generally remains outside the body of a patient and is furthest form the operating location. It is the tube end which is closest to the source of the cleavage solution and to the source of high frequency AC electrical power. By analogy, every time the terms "distal" and "proximal" are used herein, they refer to a location closest to the distal end and proximal end of the tube, respectively.

The electro-chemical surgical instrument according to the invention combines two functions: the electric knife and the chemically assisted mechanical dissector. The electric knife is commonly used in surgery. An electric knife cuts through organic tissues (hereinafter tissues) by burning organic material by the heat generated by the AC current at the electrode or in the tissue in closest contact with the electrode. Although high accuracy of the cutting patterns can be achieved with electric knives, they can cause bleeding wounds which need be cauterized rapidly and cleaned to guarantee good visibility to the surgeon throughout an operation. The burning of tissues by the electrode may extend by thermal conductivity beyond the target tissues strictly required to be removed causing wounds in healthy tissue, which need to scarify.

In one advantageous application of the electro-chemical dissector of the present invention, the chemical function thereof can be used by locally applying a cleavage solution to a target tissue to be removed, so as to define a plane of cleavage at least partially separating the target tissue from healthy tissue. The electrical function can be applied subsequently to burn the tissues to be removed. Because they are physically separated by a small gap along the plane of cleavage, the heat generated by the electric knife cannot extend by conduction to healthy tissue and only the tissue to be removed are burnt and removed.

Chemical dissectors use a cleavage solution such as MESNA able to break disulphide bonds of polypeptide chains and proteins bonding two tissues along a plane of cleaving. Very small amounts of cleavage solution are applied locally to create a gap along a cleavage plane. This means that though the gap may be defined, the tissues may still be tied to one another across the gap either by chemical bonds little sensitive to the cleavage solution, or which have not been exposed sufficiently to said cleavage solution. The separation of the target tissue can therefore be traumatic if these bonds need be broken by pulling the target tissue off the healthy tissue.

Another advantageous application of the electro-chemical dissector of the present invention, consists of using the chemical function of the electro-chemical dissector to form a gap along a plane of cleavage, followed by applying the electric knife through said gap to burn any remaining bonds bridging across the gap. This way, the target tissue can be removed cleanly and smoothly.

A chemically assisted mechanical dissector acts along planes of cleavage which are naturally there, but not necessarily visible to a surgeon prior to the formation of a gap. For this reason, the cleavage solution may initiate a gap along a plane of cleavage at a position not fully controlled by the surgeon.

In yet another advantageous application of the electro-chemical dissector of the present invention, the electric knife can be used first to form an initiating pre-cut exactly where the surgeon wishes. The cleavage solution can then be applied into said initiating pre-cut to disrupt any disulphide bonds of polypeptide chains and proteins along a plane of cleavage located in the area of the initiating pre-cut.

Because the cleavage solution does not affect blood vessels a chemical dissector is particularly suitable for detaching tissues adjacent to blood vessels. By contrast, the risk of damaging such vessels with an electric knife would be much higher, thus causing hemorrhages.

The foregoing advantageous applications of the electro-chemical dissector of the present invention could not be applied by using separate chemical and electric knives, because exactly the same position must be maintained at the distal end of the knives when using a chemical or an electric knife, which is impossible to ensure if one knife must be removed from the operation site and replaced by another. With an electro-chemical dissector of the present invention, the conductive mechanical instrument does not move when passing from a chemically assisted mechanical dissector mode to an electric knife mode and inversely, permitting to profit of the advantages of each technique without having to support their drawbacks. An additional advantage of the electro-chemical dissector of the present invention over using alternatively an electric knife and a chemical dissector, regardless of the accuracy of the positioning of the conductive mechanical instrument thereof discussed supra, is a substantial saving of time and storing place, as a single instrument is used instead of two, and it needs not be removed from the operation site when passing from one function to another.

Figure 4:
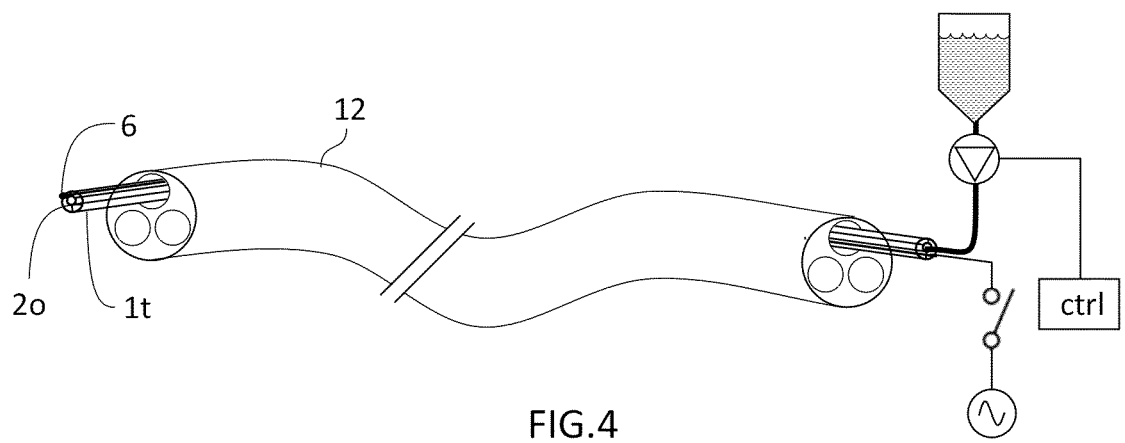
FIG. 4 shows an electro-chemical dissector according to the present invention implemented with an endoscope.

The electro-chemical surgical instrument according to the invention can be used in endoscopic surgery, in laparoscopic surgery, or in open surgery. The tube can be flexible, rigid or having portions which are flexible and portions which are rigid. As shown in FIG. 4, in endoscopic surgery, the tube, 1t, is inserted into a channel of an endoscope, 12. Other channels may comprise a camera, stitching means, and any other tools generally used in endoscopic surgery. Because the endoscope is inserted into a natural orifice such as mouth, nostril, urethra, anus, the tube is preferably partially or totally flexible. In laparoscopic and open surgery, the tube is preferably at least partially rigid, and often rigid over the whole length thereof to permit an accurate control of the distal end of the tube in the operation site.

Contrary to the electric knives provided with a channel for delivering a fluid described in EP2419038 and EP2896379, the cleavage solution in the electro-chemical dissector of the present invention must be delivered at very low volumes and pressure. The mean cross-sectional diameter, d, of the channel is therefore very small, and can be lower than 2 mm, preferably lower than 1 mm. The diameter is preferably such that capillary forces are sufficient to prevent any dripping of the cleavage solution from the channel outlet even when the channel is held vertically with the outlet pointed downwards.

Figure 2:
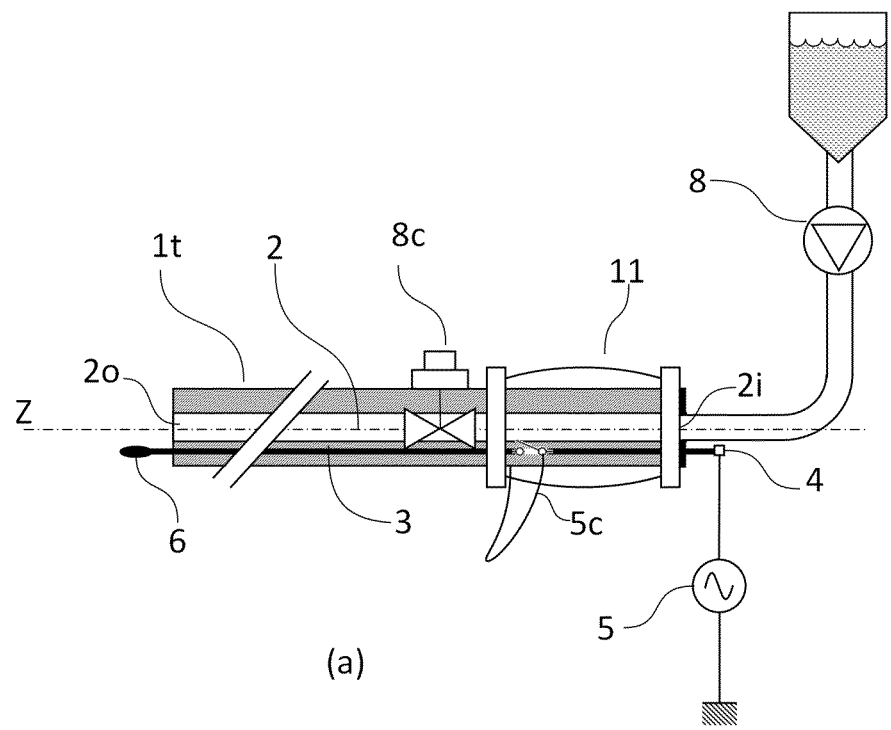
FIG. 2 shows further embodiments of electro-chemical dissectors according to the present invention.
Figure 2:
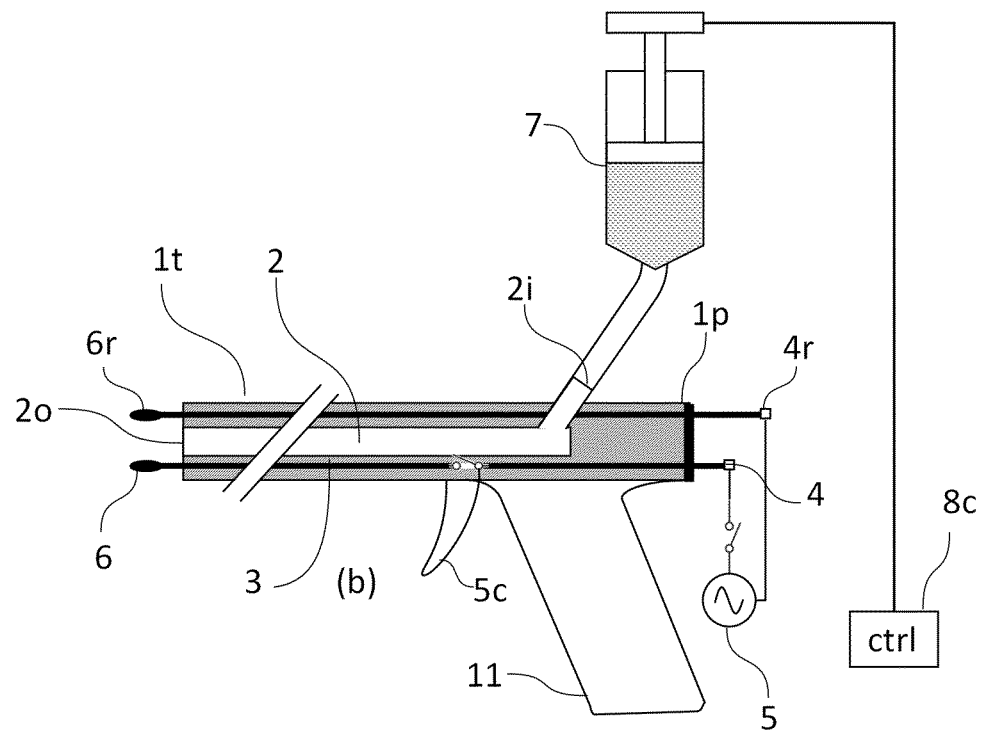
Figure 3:
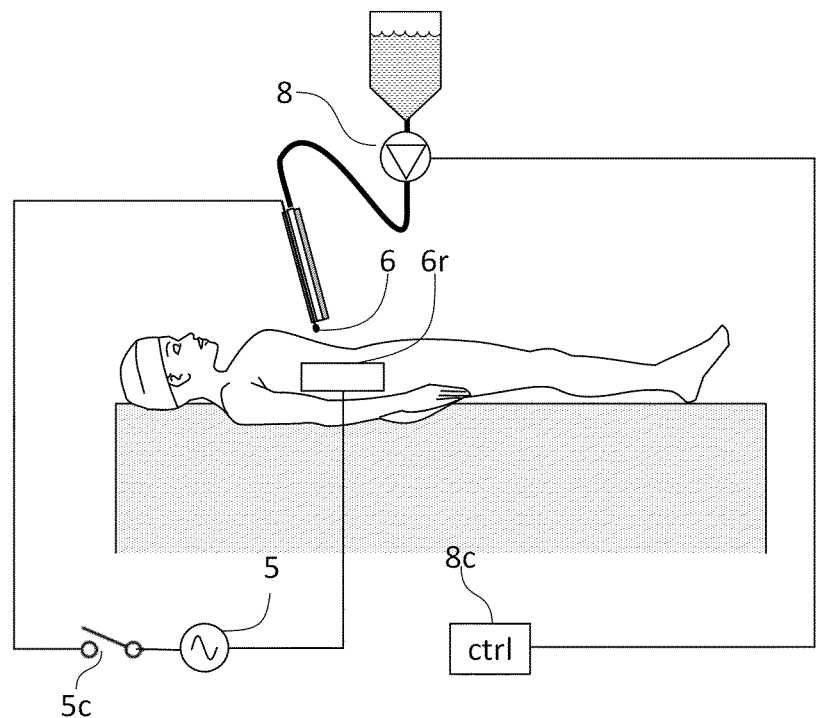
FIG. 3 shows an embodiment of electric and cleavage solution control circuits in operating conditions for a monopolar electro-chemical dissector according to the present invention.

The electric knife function can be fulfilled by a monopolar knife, comprising a single electrode, 6, at least partially formed by the conductive mechanical instrument, as illustrated in FIGS. 1(a) and 2(a). As shown in FIG. 3, a return electrode or dispersive electrode, 6r, is required. In such configuration, the electrode, 6, of the instrument forms an active electrode and a return electrode can be pasted on or coupled to the body of a patient, as illustrated in FIG. 3. In FIG. 3, both active electrode, 6, and return electrode, 6r, are coupled to the source of high frequency AC current, forming a closed electric circuit.

Alternatively, the electric knife function can be fulfilled by a bipolar knife, comprising two electrodes, 6, 6r. A first electrode, 6, is provided at the distal end of an electric conductor, 3, as discussed in reference of a monopolar knife. A second electrode, or return electrode, 6r, is provided at the distal end of a return electric conductor, 3r, which extends from said distal end to a return connection end, comprising a return connector, 4r, for connecting the return electric conductor to the source of electrical power. The return electric conductor, 3r, is at least partially housed in the tube, 1t, and the return electrode, 6r, is separated from the first electrode, 6, by a distance which can generally be varied. For example, the electrodes of a bipolar knife can move towards one another to pinch a target tissue to be removed, in the same way as the jaws of a small pliers. A closed electric circuit is thus formed including the target tissue sandwiched between the two electrodes, which can then be burnt and removed.

The electrode/conductive mechanical instrument can have a variety of geometries, which depend on whether the electric knife is monopolar or bipolar, on the type of tissue to be cut, on the desired cutting pattern, and on the type of surgery. Indeed, because the angular orientation about the longitudinal axis, Z, of the distal end of a tube cannot be accurately controlled in endoscopic surgery, electrodes for endoscopic surgery preferably have a geometry which is substantially of revolution about the longitudinal axis, Z.

For example, as illustrated in FIG. 5(a) to (d), an electrode/conductive mechanical instrument, particularly suitable, but not exclusively, for endoscopic surgery may comprise a cylindrical portion defining a lateral surface and a distal end portion generally in the shape of a spherical or elliptical cap. The distal end portion can be more or less elongated and the radius of the cylindrical portion may vary depending on the particular applications. A typical endoscopic electrode can have a cylindrical portion of diameter lower than 1 mm, preferably lower than 0.5 mm.

The electrodes/conductive mechanical instrument, however, do not necessarily have a geometry of revolution about the longitudinal axis, Z. This is clearly the case in laparoscopic and open surgeries, since the position and orientation of the distal end of the tube are controlled directly and accurately by the hand of a surgeon. It can also be the case in endoscopic surgery, as devices are available allowing an enhanced control of the position of an endoscopic tool. For example, WO2015/052320 describes a device for supporting an endoscopic tool giving additional degrees of liberty to the controlled motion of an endoscopic tool. Without the constraint of using a geometry of revolution, all kinds of geometries are of course available which are best suited for each type of intervention.

Examples of non-axisymmetric electrode/conductive mechanical instrument geometries are illustrated in FIG. 6(a) to (d). The electrode illustrated in FIG. 6(a), (b) & (c) is generally in the shape of a spatula, a spoon, a blade, or a hook with edges which can be more or less sharp or blunt. The conductive mechanical instrument may be defined by two lateral surfaces separated from one another by the thickness of the conductive mechanical instrument. As shown in FIG. 6(a)&(b), one lateral surface may comprise a recessed hollowness facing the outlet of the channel to receive a volume of cleavage solution.

Figure 5:
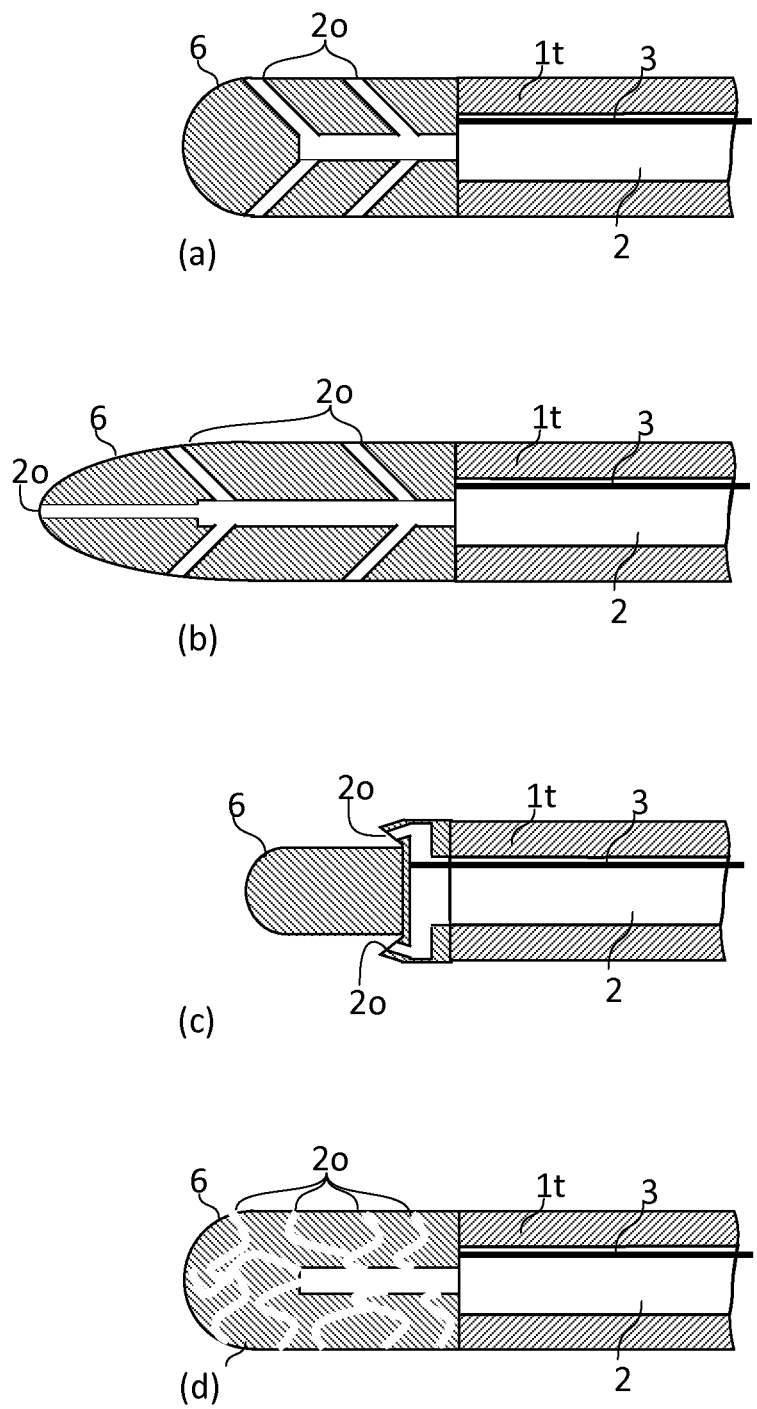
FIG. 5 shows various geometries of electrodes/conductive mechanical instruments preferably for endoscopic surgery.
Figure 6:
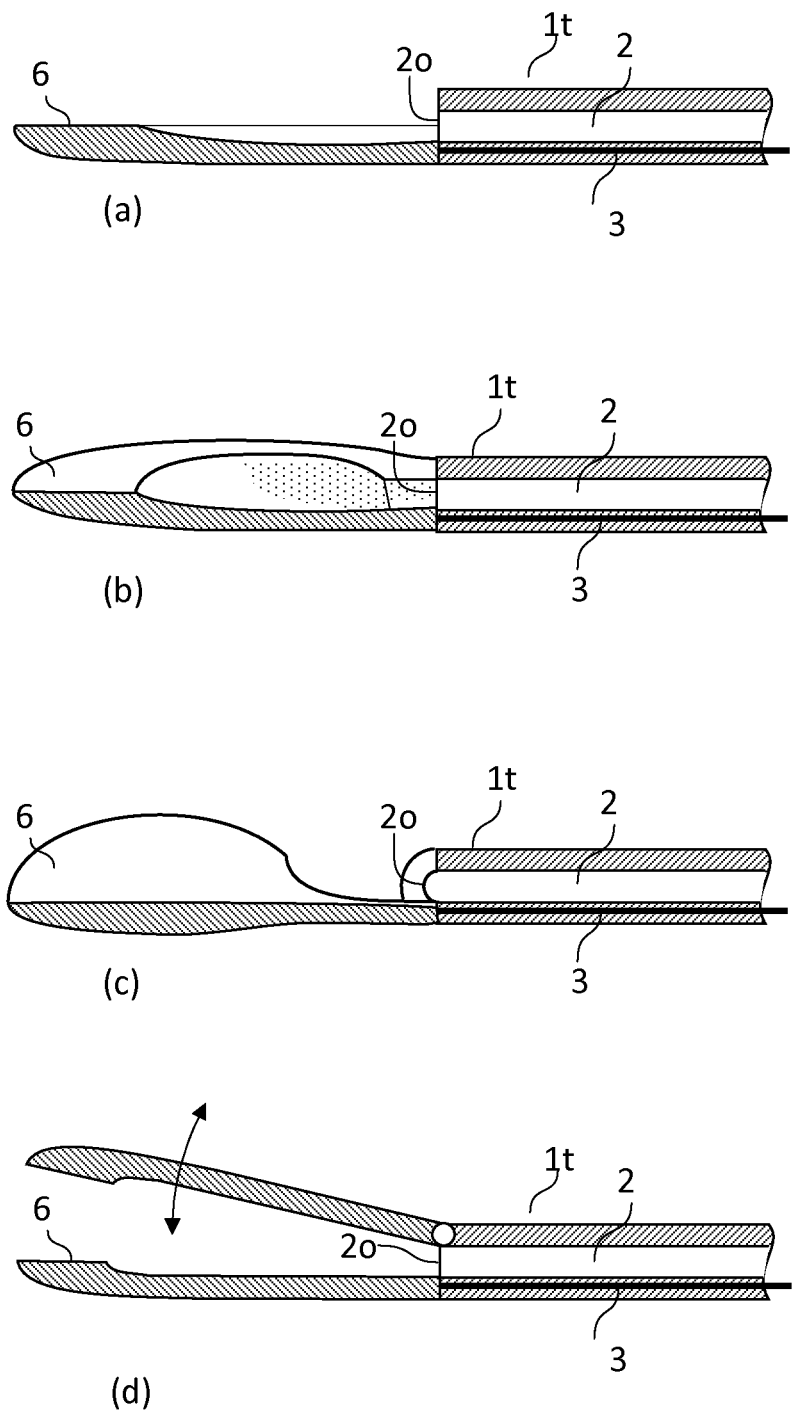
FIG. 6 shows various geometries of electrodes/conductive mechanical instruments preferably for laparoscopic or open surgery.

The electrodes preferably have in common that they all comprise at least one lateral surface non-normal to, and preferably substantially parallel to the longitudinal axis. The channel outlet preferably opens at said lateral surface, as illustrated in FIG. 5(a), (b) & (d), or is adjacent to and aims at said lateral surface as illustrated in FIG. 5(c) and FIG. 6. The channel outlet does not form a needle and cannot penetrate through a tissue. The channel outlet is designed for applying cleavage solution onto the lateral surface of the electrode and onto the surface of the tissues to be treated, but not through such tissues.

The source of cleavage solution can be any type of vessel, including a cartridge, a pouch, a bottle, a bag-in-box type of container, or a syringe. A syringe can act both as source of cleavage solution and a pump. The cleavage solution can be, for example, sodium 2-mercatoethanesulfonate (MESNA), N-acetylcysteine, dithiothreitol (DTT), β-mercaptoethanol or free cysteine. Sodium 2-mercatoethanesulfonate (MESNA) is preferred.

A pump, 8, is required to deliver precise volumes of cleavage solution to the pressurized operation site. Because the cleavage solution must be delivered in small, albeit accurate quantities, a volumetric pump is preferred. For example, the pump, 8, can be a peristaltic pump, a syringe or a piston pump. A volumetric pump is preferred because the control of the pressure is secondary, as long as it is greater than the pressure reigning in the operation site. The volume dispensed by the pump, however, must be controlled very accurately. Alternatively, a pressurized gas can be injected into the vessel containing the cleavage solution. To prevent any contact between the pressurized gas and the cleavage solution, a bag-in-box type of container can be used, such as described in EP2148770. The pressurized gas can be stored in a pressure bottle, adsorbed on a solid carrier, or generated by a compressor.

Typically, the cleavage solution can be dispensed in shots of volume comprised between 0.1 and 1 ml. The pressure developed by the pump can be less than 2 bar, preferably less than 1 bar, more preferably not more than 0.5 bar over atmospheric pressure (=1013.25 mbar).

As illustrated in FIG. 6(d), the conductive mechanical instrument of the electro-chemical instrument of the present invention may form forceps or a Maryland dissector as follows. The conductive mechanical instrument can comprise a pair of first and second jaw members. At least one of the first and second jaw members is movable from an open configuration to a clamping configuration to form the forceps or a Maryland dissector. The first jaw member is formed by the electrode, 6. The second jaw may or may not form a return electrode, 6r, coupled to the source of high frequency AC current. If it is not coupled thereto, monopolar electrosurgical forceps or a monopolar Maryland dissector are formed. If it is coupled thereto, the second jaw forms the return electrode and bipolar electrosurgical forceps or a bipolar Maryland dissector are formed. The forceps or Maryland dissector can be a non-locking or locking forceps or Maryland dissector. The locking forceps or Maryland dissector can be used to lock the grasping surfaces in a closed position to facilitate manipulation or to independently clamp, grasp or hold an object or tissue.

The electric controller, 5c, consists of a switch. It can be an on/off switch or it may be a dimmer with a varying resistance, which allows the control of the amount of current fed to the electrode at any moment. The electric controller is generally in the form of a footswitch, which can be controlled by the surgeon with its foot (cf. FIG. 3). Alternatively, the electric controller can be in the form of a finger trigger or push button positioned near the tube proximal end, for example at a handle, 11, as shown in FIG. 2. The handle can be coaxial with the longitudinal axis, Z, forming a sword grip as illustrated in FIG. 2(a). Alternatively, the handle can be transverse to the longitudinal axis, Z, forming a gun grip handle, as shown in FIG. 2(b). A handle is generally used for electro-chemical instruments for laparoscopic and open surgeries, as the instrument is controlled directly by the hand of a surgeon.

The flow controller, 8c, controls the flow of cleavage solution by controlling the actuation of either the pump, 8, as shown in FIGS. 1(b) and 2(b), or a valve, 8v, located downstream from the pump, as shown in FIGS. 1(a) and 2(a). In case of electrically actuated pumps or valves, the flow controller can be an electric switch. Like the electric controller, such electric switch can be an on/off switch or it may be a dimmer with a varying resistance, which allows the control of the volume of cleavage solution fed to the channel at any moment. The flow switch can be in the form of a footswitch, which can be controlled by the surgeon with its foot (cf. FIG. 3). Alternatively, the flow controller can be in the form of a finger trigger or push button positioned near the tube proximal end, for example at a handle, 11, as shown in FIG. 2. Alternatively, the pump or valve can be actuated mechanically, such as to push the piston of a syringe down (cf. FIG. 2(b)) which can be actuated manually, pneumatically, hydraulically, or electrically. Similarly, a pinch valve can be actuated manually by controlling the cross-sectional area of a flexible portion of the channel pinched between to moving jaws of the pinch valve.

The channel outlet, 2o, is important as the cleavage solution is preferably dispensed in small amounts and at very specific locations. For an optimal synergy between the chemical and electric knives, the channel outlet is oriented such as to wet a lateral surface of the conductive mechanical instrument. As shown in FIG. 5(a)&(b) the channel may open at a lateral surface of the conductive mechanical instrument. FIG. 5(a)&(b) illustrates endoscopic electrodes/conductive mechanical instrument, but the same can apply to electrodes for laparoscopic or open surgery too. Alternatively, or additionally, the channel may also comprise an outlet oriented parallel to the longitudinal axis, Z, and, as illustrated in FIG. 5(b), opening at or adjacent to a distal end of the electrode/conductive mechanical instrument. The lateral surface of the electrode can also be porous, and the channel outlets are formed by the open porosity of the electrode, as illustrated in FIG. 5(d).

Alternatively, the channel may open adjacent to the lateral surface. It is preferred that in this case, the one or more channel outlets be oriented such as to dispense the cleavage solution onto a lateral surface of the electrode/conductive mechanical instrument, which can be used to mechanically assist in the separation of the tissues. FIG. 5(c) illustrates an electrode suitable for endoscopic surgery, wherein the channel outlets are distributed around the lateral surface of the electrode and are pointed towards said lateral surface. Several such outlets can be distributed around the lateral surface, or a ring-shaped opening can be considered instead.

FIG. 6 illustrates electrodes more suitable for laparoscopic and open surgeries, with the channel opening oriented such as to dispense the cleavage solution onto a lateral surface of the electrode.

In the case where the electrode/conductive mechanical instrument is in the shape of a spatula, a scoop or scoopula having two lateral surfaces, the channel outlet(s) may be oriented such as to wet one of the two lateral surfaces only, or both lateral surfaces simultaneously. For the latter, two channel outlets facing the two lateral surfaces can be used or, alternatively, a single channel outlet may open coaxially with the longitudinal axis, Z, and parallel to the two lateral surfaces separated by the thickness of the conductive mechanical instrument, said outlet having a diameter larger than the thickness of the conductive mechanical instrument and opening at both lateral surfaces.

An electro-chemical surgical instrument according to the present invention can be used for delivering a cleavage solution stored in the source of cleavage solution (7) as follows:

(a) connecting the connection end of the electric conductor to a source of high frequency AC electrical power; the instrument is thus ready for use as an electric knife, and (b) by means of the flow controller (8c), actuating the pump (8) or a valve (8v) located downstream from the pump to feed the cleavage solution from the source of cleavage solution to the outlet of the channel, so that the instrument is used as chemical dissector.

By actuating the electrical and flow controllers (5c, 8c) alternatively or simultaneously, the electro-chemical surgical instrument of the present invention can be used in a number of configurations which could not be envisaged to date. First, the surgical instrument can be used to remove a target tissue using either the electric knife only or the chemically assisted mechanical dissector only, both functions being present and ready for use in a single instrument. More advantageously, both electrical and chemical dissectors can be used sequentially to remove different tissues. This is already advantageous, because a surgeon needs not remove one knife and introduce a second knife, and can simply switch from one type of knife to the other by actuating the flow controller or the electric container, sequentially.

The electro-chemical surgical instrument of the present invention, however, is most advantageously used by using both electrical and chemical dissectors on a same target tissue to profit of the advantages of each technique without having to support their drawbacks. For example, the chemically assisted mechanical dissector can be used to first create a gap along a plane of cleavage, partly separating a target tissue from healthy tissue. Immediately after, the electric knife can be used to burn the target tissue, without damaging healthy tissues thermally protected by the gap from the heat generated by the electrode. This combination of two techniques is more advantageous than each technique used on its own, and avoids any of their inconveniences.

In another application, the electric knife can be used to create a pre-cut in the approximate area where a plane of cleavage is expected. The chemically assisted mechanical dissector can be used immediately after to deposit some cleavage solution in the pre-crack and thus attack the polypeptide chains and proteins along the nearest cleavage plane to the pre-crack. This way, a most accurate chemical separation can be achieved, that was not hitherto possible by using a chemically assisted mechanical dissector alone.

Another advantageous technique is to start a chemical separation along a plane of cleavage with lower amounts of cleavage solution than normally required. Some polypeptide chains and proteins may thus resist the chemical separation. Without moving the instrument from its position, said resisting chains and proteins can be cut electrically by switching the electric knife on. This way, lower amounts of cleavage solution are required, and shorter operating times can be achieved.

For any of the foregoing combined techniques switching from a chemically assisted mechanical dissector to an electric knife, it is possible to rapidly and repeatedly switch from a chemically assisted mechanical dissector to an electric knife and back to a chemical dissector, as the separation is progressing through a tissue. The two functions can even be applied simultaneously, with small amounts of cleavage solution being applied to a freshly burnt tissue as the electric knife is progressing along the cutting trajectory, so that the resistance of the tissues to the electric knife is substantially decreased by the chemical attack to the proteins bonding tissues together. If the electrode forms one jaw of a forceps or of a Maryland dissector, another function can be advantageously implemented with the present electro-chemical surgical instrument, allowing the removal of cut off tissue, as samples or simply for clearing the operating site.

Rapid switching from electrical to chemical cutting functions is rendered very easy by simply sequentially actuating the electric controller, 5c, and the flow controller, 8c, for example with a foot, in case one or both electric and flow controllers are foot pedals (cf. FIG. 3), or with a finger, in case one or both electric and flow controllers are finger triggers or push buttons (cf. FIG. 2). Simultaneous activation of the electric and chemical dissectors can be achieved by simply actuating both electric and flow controllers simultaneously. In another embodiment, the electric knife can be activated continuously, and little bursts of cleavage solution can be discharged intermittently to assist the cutting operation.

None of the foregoing combined uses of an electric knife and a chemically assisted mechanical dissector would be possible without an electro-chemical surgical instrument according to the present invention, because it would be impossible to reach with a new instrument the exact spot where an instrument recently retrieved from the operating area has been used last. It would be extremely difficult to use an electric knife, retrieve it, introduce a chemically assisted mechanical dissector and find the exact spot of the last intervention, and use the chemical dissector. This would already be cumbersome when done once. It would be unthinkable to repeat such actions several times during a same intervention.

In open surgery, a slit opening is first cut at the skin surface in a conventional manner to give access to the operating site. Once the tissue to be removed is exposed, an electro-chemical surgical instrument according to the present invention can then be inserted into the operating site as any other surgical instrument. The electro-chemical surgical instrument can then be used as described above, as an electric knife to burn the target tissue to be removed, as a chemically assisted mechanical dissector to separate the target tissue from the healthy tissue along a plane of cleavage, or simultaneously as an electro-chemical dissector for proceedings with the cutting pattern by locally burning and separating along planes of cleavage the target tissue to be removed.

Another example of use of the present invention is for cutting a portion of an organ such as liver. The liver is surrounded by a layer of protective tissue which is resistant to cleavage solutions and can thus be cut with the electric knife. Once this layer of protective tissue has been cut through, exposing the surface of the liver, a cleavage solution can be used to detach target tissues from healthy tissues within the liver.

In a corresponding manner, the electro-chemical surgical instrument according to the present invention can be used in laparoscopic surgery. In this kind of surgery, one or more slit openings of small dimensions are cut at the surface of the skin, for allowing the insertion of trocars to reach the operating site. The electro-chemical surgical instrument can be introduced through a trocar down to the operating site. A surgeon can visualize the operating site with a camera. Else the electro-chemical surgical instrument is used in laparoscopic surgery much in the same way as in open surgery.

In both open and laparoscopic surgeries, the surgical instruments are controlled directly by the hands of a surgeon, and the position and orientation of the distal end of an instrument, like the electrode and the channel opening for electro-chemical surgical instruments, can be controlled very accurately. The distal end can therefore have a variety of geometries which are specific to the type of operations. FIG. 6 illustrates some examples of such geometries, including an electrode in the shape of a spoon or spatula in FIGS. 6(a), (b) & (c), and an electrode forming one jaw of a forceps in FIG. 6(d).

Finally, the electro-chemical surgical instrument according to the present invention can be used in endoscopic surgery. In this case, as shown in FIG. 4, the instrument in inserted in a lumen of an endoscope. The endoscope is introduced in an orifice of the body to reach the operating site without cutting any slit at the surface of the skin. The handling of the distal end of the electro-chemical surgical instrument through the lumen of an endoscope is not as accurate as in open or laparoscopic surgeries. For example, it is difficult to accurately control the angular orientation about the longitudinal axis of the distal end of the instrument. This explains that the electrode geometries for endoscopic instruments preferably is substantially a geometry of revolution about said axis, as shown in FIG. 5 and discussed supra.

The handling of a surgical instrument through an endoscope can be enhanced with special supporting devices, such as described in WO2015/052320. If such supporting devices afford a sufficient control of the position and orientation of the distal end of the electro-chemical surgical instrument, the geometry of the electrode can be more freely designed, as discussed with respect to open and laparoscopic surgeries.

Because the operating site is often slightly over-pressurized with respect to the atmospheric pressure reigning outside the body of a patient, the cleavage solution must necessarily be dispensed with a pressure above both atmospheric pressure and the pressure inside the operating site. The cleavage solution needs only be dispensed in small but very accurate volumes, at a pressure sufficient for overcoming the pressure in the operating site. The pressurization and dispensing of the cleavage solution can be controlled by a pump, 8, only; by a pump and a valve, 8v, located downstream of the pump; or by a valve, 8v, disposed downstream of a source of pressurized gas which pressurizes the cleavage solution in the source, 7. Advantageously, the cleavage solution can be stored in the bag of a bag-in-box vessel, and the pressurized gas is injected between the bag and the box. This way, the cleavage solution is pressurized without any contact with the pressurizing gas. The pump or valve can be actuated by means of the flow controller, $8c$, as explained supra.

A new range of applications for non-traumatic separation of target tissues from healthy tissue is opened by the electro-chemical surgical instruments of the present invention. At least two functions, electric burning and chemical separation along cleavage planes of target tissues can be used alternatively, sequentially, or simultaneously, to profit of the advantages of one technique, while avoiding the drawbacks of the other. Other cutting functions can be implemented in the present electro-chemical surgical instrument, such as handling functions by means of a forceps or a Maryland dissector. The polyvalence and versatility of the present electro-chemical surgical instrument constitutes a breakthrough in surgical instruments.

| # | FEATURE |
|---|---|
| 2 | Channel |
| 3 | Electric conductor |
| 4 | Electric connector |
| 5 | Source of high frequency AC current |
| 6 | Electrode/conductive mechanical instrument |
| 7 | Source of cleavage solution |
| 8 | Pump |
| 11 | handle |
| 12 | Endoscope |
| 1t | Tube |
| 2i | Channel inlet |
| 2o | Channel outlet |
| 3r | return electric conductor |
| 4r | Return electric connector |
| 5c | Electric controller |
| 6r | Return electrode |
| 8c | Flow controller |
| 8v | Valve |
| D | Channel diameter |
| L1 | Tube length |
| L2 | Length of housed portion of channel |
| Z | Longitudinal axis |

The invention claimed is:

1. An electro-chemical surgical instrument for separating target tissues in an operating site, said electro-chemical surgical instrument comprising:
   (A) a chemically assisted mechanical dissector for removing the target tissues, comprising:
      (a) an electrically conductive mechanical dissector instrument configured for exerting a separation force on the target tissues to be dissected and having one of the following geometries: a blade, a spatula, a spoon, a forceps, or a Maryland dissector, the electrically conductive mechanical instrument being coupled to a distal end of,
      (b) a tube (1t) which is non-conductive and extends over a length, L1, measured parallel to a longitudinal axis, Z, from a proximal end to the distal end;
      (c) a source (7) of a cleavage solution containing sodium 2-mercaptoethanesulfonate (MESNA) able to break disulphide bonds of polypeptide chains and proteins, which is fluidly coupled through a pump to an inlet (2i) of,
      (d) a channel (2) extending from the inlet (2i) to one or more channel outlets (2o), having a housed portion of length, L2, which is housed in the tube with said one or more channel outlets being located at or adjacent to the distal end, configured to wet a lateral surface of the electrically conductive mechanical instrument with the cleavage solution when the pump is activated;
      (e) a flow controller (8c) configured for activating the pump and thus feeding the cleavage solution to the one or more channel outlets; and
   (B) an electric knife for cutting and/or cauterizing the target tissues, comprising:
      (f) an electric conductor (3) extending from a connection end comprising a connector (4) for connecting the electric conductor to a source (5) of radio frequency AC electrical power, for feeding electrical power to an electrode end comprising an electrode (6) formed by the electrically conductive mechanical instrument, wherein a portion of said electric conductor is housed in the tube; and
      (g) an electric controller (5c) configured for controlling the feeding of the electrical power current to the electrode.

2. The electro-chemical surgical instrument according to claim 1, wherein the one or more channel outlets of the chemically assisted mechanical dissector are oriented such as to dispense the cleavage solution onto the lateral surface of the dissector.

3. The electro-chemical surgical instrument according to claim 1, wherein the electric knife comprises either:
   solely the electrode formed by the electrically conductive mechanical instrument at the electrode end of the electric conductor, thus forming a monopolar electric knife, or
   further comprising a return electrode (6r) at a return electrode end of a return electric conductor (3r) forming together with the electrode at the electrode end of the electric conductor a bipolar electric knife.

4. The electro-chemical surgical instrument according to claim 1, wherein the electrically conductive mechanical instrument comprises a pair of first and second jaw members, at least one of the first and second jaw members being movable from an open configuration to a clamping configuration, the first jaw member including the electrode, thus forming a monopolar electrosurgical forceps or a monopolar Maryland dissector.

5. The electro-chemical surgical instrument according to claim 4, wherein the electric knife comprises a return electrode (6r) at a return electrode end of a return electric conductor (3r) forming together with the electrode at the electrode end of the electric conductor a bipolar electric knife, and wherein the second jaw member includes the return electrode, thus forming a bipolar electrosurgical forceps.

6. The electro-chemical surgical instrument according to claim 1, wherein the electric controller comprises a switch trigger for controlling the feeding of the electrical power to the electrode.

7. The electro-chemical surgical instrument according to claim 6, further comprising a handle (11), and wherein the switch trigger is a pushbutton switch located on the handle or a footswitch.

8. The electro-chemical surgical instrument according to claim 1, wherein the flow controller comprises a flow trigger for controlling the pump or a valve located downstream from the pump, to feed the cleavage solution to the one or more channel outlets.

9. The electro-chemical surgical instrument according to claim 8, further comprising a handle (11), and wherein the flow trigger (8c) is a pushbutton switch located on the handle.

10. The electro-chemical surgical instrument according to claim 1, wherein the pump of the chemically assisted mechanical dissector is selected from: a peristaltic pump, a syringe, or a piston pump, and wherein the pump pressurizes the cleavage solution at a maximum pressure of not more than 2 bar.

11. The electro-chemical surgical instrument according to claim 1, wherein the tube of the chemically assisted mechanical dissector is at least partly rigid.

12. A method for dissecting a tissue in surgery comprising the following steps with the electro-chemical surgical instrument of claim 1, the method comprising:
 (a) combining an application of the cleavage solution containing sodium 2 mercaptoethanesulfonate (MESNA) with an application of the separation force by the electrically conductive mechanical instrument to detach the tissue;
 (b) cutting the tissue which cannot be detached in step (a) by applying an electric RF field through the electrode end; and
 (c) cauterizing any bleeding that may arise by application of the electric RF field through the electrode end.

\* \* \* \* \*